United States Patent [19]

Weferling et al.

[11] Patent Number: 4,757,156
[45] Date of Patent: Jul. 12, 1988

[54] PROCESS FOR MAKING TERTIARY ALKYLPHOSPHINES

[75] Inventors: Norbert Weferling; Georg Elsner; Hans-Werner Stephan; Friedrich-Karl Frorath, all of Hürth, Fed. Rep. of Germany

[73] Assignee: Hoechst Aktiengesellschaft, Fed. Rep. of Germany

[21] Appl. No.: 85,853

[22] Filed: Aug. 14, 1987

[30] Foreign Application Priority Data

Aug. 28, 1986 [DE] Fed. Rep. of Germany ....... 3629189

[51] Int. Cl.$^4$ ................................................. C07F 9/50
[52] U.S. Cl. ......................................................... 568/8
[58] Field of Search ............................................. 568/8

[56] References Cited

U.S. PATENT DOCUMENTS

| | | | |
|---|---|---|---|
| 2,584,112 | 2/1952 | Brown | 568/8 |
| 2,803,597 | 8/1957 | Stiles et al. | 568/8 X |
| 2,822,376 | 2/1958 | Hechenbleikner et al. | 568/8 X |
| 4,073,810 | 2/1978 | Hestermann et al. | 568/8 |
| 4,163,760 | 8/1979 | Elsner et al. | 260/606.5 P |
| 4,324,919 | 4/1982 | Elsner et al. | 568/8 |

FOREIGN PATENT DOCUMENTS

| | | | |
|---|---|---|---|
| 0095453 | 11/1983 | European Pat. Off. | 568/8 |
| 899040 | 12/1953 | Fed. Rep. of Germany | 568/8 |
| 2703802 | 11/1978 | Fed. Rep. of Germany | 568/8 |
| 2936210 | 3/1981 | Fed. Rep. of Germany | 568/8 |

OTHER PUBLICATIONS

Rauhut et al, "The Free Radical Addition of Phosphines to Unsaturated Compounds", Journal of Organic Chemistry (1961) vol. 26, pp. 5138–5145.

*Primary Examiner*—Paul F. Shaver

[57] ABSTRACT

Tertiary alkylphosphines of the general formula $R_3P$, in which R stands for identical or different, linear, unsubstituted alkyl groups having 3 to 20 carbon atoms, with the proviso however that one of the alkyl groups may be a secondary butyl group, are made by reacting hydrogen phosphide $PH_3$ with an appropriate alkene or alkenes in stoichiometric excess, if desired, at elevated temperature and under increased pressure in contact with a radical-yielding agent. 2,2'-azobis-(2-methylbutyronitrile) is used as the radical-yielding agent in the absence of whatever alien solvent.

9 Claims, No Drawings

PROCESS FOR MAKING TERTIARY ALKYLPHOSPHINES

The present invention relates to a process for making tertiary alkylphosphines of the general formula $R_3P$, in which R stands for identical or different, linear, unsubstituted alkyl groups having 3–20, preferably 4–10, carbon atoms, where a secondary butyl group may however stand for one of the alkyl groups, by reacting hydrogen phosphide $PH_3$ with an appropriate alkene or alkenes in stoichiometric excess, if desired, at elevated temperature and under increased pressure in contact with a radical donator.

In German Specification No. DE-PS 899 040 it has already been disclosed that equivalent quantities of hydrogen phosphide and an olefin can be reacted at elevated temperature in contact with a peroxidic catalyst. In Example 2 of that specification, a mixture of about 85 wgt % trialkylphosphine and about 15 wgt % mono- or dialkylphosphine is obtained.

In Journal of Organic Chemistry (1961), volume 26, page 5139, it has been reported that the use of a stoichiometric excess of hydrogen phosphide permits the formation of the trialkylphosphine to be repressed in favor of the formation of di- or monoalkylphosphine.

German Specification No. DE-PS 27 03 802 discloses a process for making organic phosphines from an alkene solution which is reacted with a stoichiometric excess of hydrogen phosphide in a continuously operated autoclave. A further process for making tertiary phosphines has been disclosed in German Specification No. DE-OS 29 36 210, which is also carried out in the presence of an inert solvent, such as toluene, under pressure, at increased temperatures and with the use of azobisisobutyronitrile in toluene as an initiator solution.

A still further process has been disclosed in European Specification No. EP-A2 0 095 453, wherein hydrogen phosphide is reacted at 85°–90° C. with butene-2 with the use of a solution of azobisisobutyronitrile in toluene as a radical-donator.

All of these processes are not free from adverse effects. The azobisisobutyronitrile (ABIN) customarily used heretofore as a radical-donator invariably calls for the use of one or more alien solvents. The solvents useful for ABIN just comprise toluene and benzene in which the starter or initiator is dissolved. In addition, very toxic tetramethyl succinic acid dinitrile ($LD_{50}$ per inhal. 6 mg/kg rat (30 hours); per os about 25 mg/kg rat) is obtained as a decomposition product of ABIN. The use of alien solvents implies using additional storage tanks, pumps, dosing means and distilling facilities for recovery, and this naturally means considerable investment costs.

The disadvantages associated with the above prior processes can unexpectedly be avoided by using 2,2'-azobis(2-methylbutyronitrile) as the radical-donator in the absence of whatever alien solvent.

This enables the above disadvantages to be set aside without any additional depense; as already stated above, the present process avoids the need to use an alien solvent and consequently the need to work-up such acid. In addition, less initiator is used; in the prior processes ABIN is used at a rate of about 3 mol %, based on $PH_3$; in the present process, 2,2'-azobis-(2-methylbutyronitrile) (VAZO® 67, this is a registered Trade Mark of E. I. Dupont de Nemours & Company, Wilmington, U.S.A.) is used at a rate of 1–2 mol %, based on $PH_3$. In this way, the space/time yield is generally doubled. Merely for the reaction e.g. of sec.-butylphosphine with a n-alkene in a secondary reaction stage is it necessary to use more important quantities of the novel initiator of this invention; this however is also true concerning ABIN.

Further preferred and optional features of the present invention comprise:

(a) making tertiary alkylphosphines with straight alkyl groups by reacting an alkene-1 or alkene-1 blend with $PH_3$ in a stoichiometric ratio of 3:1 to 5:1, under a pressure of 1–80 bars, at a temperature of 75°–95° C. over a mean period of 4–24 hours in contact with 0.1–2 mol % 2,2'-azobis-(2-methylbutyronitrile) based on $PH_3$, and working up the crude trialkylphosphine by distilling it;

(b) making tertiary alkylphosphines one of the alkyl groups of which is a secondary butyl group in two stages by reacting, in the first stage, butene-2 with $PH_3$ in a stoichiometric excess of up to 400 mol %, based on $PH_3$, under a pressure of 35–180 bars, at a temperature of 90°–120° C. over a mean reaction period of 0.1–7 hours in contact with 1–2 mol % 2,2'-azobis-(2-methylbutyronitrile), based on $PH_3$, and distillatively purifying the s-butylphosphine obtained, and then reacting, in the second stage, the said s-butyl-phosphine with an alkene-1 or alkene-1 blend in a stoichiometric excess of up to 1000 mol % total alkene-1, based on s-butylphosphine, under a pressure of 1–3 bars, at a temperature of 75°–95° C. over a mean reaction period of 4–24 hours and in contact with 2–6 mols 2,2'-azobis-(2-methylbutyronitrile), based on s-butylphosphine, and working up the crude s-butyl-di-n-alkylphosphine by distilling it;

(c) carrying out the reaction and distilling steps continuously;

(d) dissolving the 2,2'-azobis-(2-methylbutyronitrile) in the alkene used as feed material or in the s-butylphosphine obtained as the intermediary product and thus avoiding the need to use an alien solvent;

(e) using the 2,2'-azobis-(2-methylbutyronitrile) as a 0.01–3.0 wgt % solution, preferably as an olefinic solution; and (f) separating unreacted $PH_3$, butene-2 or alkene-1 in the distilling stages, recycling the unreacted materials into the respective reaction stage.

The following Examples illustrate the invention which is naturally not limited thereto:

EXAMPLE 1

(Prior Art)

Preparation of tributylphosphine in an autoclave

A 90 liter-autoclave was charged with 9.6 kg (170 mol) butene-1 and 1.75 kg (51 mol) $PH_3$ in the sequential order indicated. Next, the autoclave was heated to 80° C. and the addition of the toluene/ABIN-solution was started. 12 l toluene in which 170 g ABIN (2 mol %, based on $PH_3$) was dissolved was pumped over a period of 2.5 hours into the reactor so that the temperature of the reaction mixture did not exceed 100° C. After a reaction period of 7½ hours, the whole was allowed to cool and the crude product (18.3 kg) was given into a barrel scavenged with nitrogen.

The following composition was determined by $^{31}$P-NMR-spectroscopy:
Tributylphosphine: 93.4 mol %, based on total P-content Dibutylphosphine: 4.6 mol %
Monobutylphosphine: 1.7 mol %
Components not identified: 0.3 mol %.

Elementary analysis indicated that the crude product contained 6.7 wgt % phosphorus. This corresponded to the conversion of 1.2 kg of the PH$_3$ used (71 % of the theoretical).

EXAMPLE 2

(Prior Art)

A pilot facility provided with an ABIN/toluene-reservoir and dosing pump, butene-1-reservoir with dosing pump, high pressure pipe (12 l filling volume) and an 800 l-stainless steel vessel with stirrer was charged continuously within 15 hours with 36 kg PH$_3$, 248 l toluene/ABIN-solution (2 wgt % ABIN) and 211.5 kg butene-1 which were introduced into the high pressure pipe. The pressure varied between 35 and 39 bars. The reaction was initiated by heating the upper portion of the column with steam (3 bars). A temperature between 125° and 140° C. was found to establish in the middle portion of the column and a temperature of 100°–120° C. in the column bottom portion. The solution of the crude product, the level of which in the column was controlled, was metered into the stainless steel reactor which contained 2 kg solid initiator and was heated to 90° C. After the whole quantities of the above materials were in the vessel with stirrer, the whole was allowed to undergo post-reaction over a period of 7 hours at 90° C. under 11–12 bars. The pressure was ultimately released and 466 kg crude product solution was obtained. The product was subjected to $^{31}$P-NMR-spectroscopy and the following result relative to the distribution of the phosphorus-containing products was obtained:

Tributylphosphine: 95.5 mol %, based on total P-content
Dibutylphosphine: 2.8 mol %
Monobutylphosphine: 0.5 mol %
Components not identified: 1.2 mol %

The crude material was worked up and 203 kg pure tributylphosphine was obtained (91%, based on PH$_3$ used). Bp 108°–112° C./10 millibars.

EXAMPLE 3

(Invention)

Semicontinuous solvent-free preparation of tributylphosphine

A solution was prepared in a 300 l-autoclave from 180 kg butene-1 and 2.8 kg 2,2'-azobis-(2-methylbutyronitrile) (VAZO® 67). The solution was metered at a rate of about 30 l/h into the upper reaction zone heated to 90° C. of the pressure pipe described in Example 2. At the same time, PH$_3$ (about 2.1 m$^3$/h) was introduced into the high pressure column. A pressure of 36 bars was found to establish. The heating and/or cooling jacket segments forming part of the reaction tube were controlled so that the reaction temperature was prevented from exceeding 90° C. The reaction solution was metered into the vessel with stirrer heated to 85° C. After 9.1 hours, the butene/initiator-reservoir was found to be empty and the introduction of PH$_3$ into the pressure pipe was stopped. The reaction mixture in the stirring vessel was allowed to undergo post-reaction over a period of 7 hours at 11 bars, then cooled and the pressure was released. 194 kg crude product was obtained. $^{31}$P-NMR-spectroscopy gave the following results:

Tributylphosphine (−32.4 ppm, −19.3 ppm): 98.5 mol %
Dibutylphosphine (−69.3 ppm): 0.4 mol %
Monobutylphosphine (−138.8 ppm): 0.3 mol %
Components not identified: 0.8 mol %

The crude product was distilled and 154 kg pure tributylphosphine (bp 105°–112° C./12 millibar) was obtained. The yield was 96%, based on the PH$_3$ used.

EXAMPLE 4

Continuous process for making trioctylphosphine 6.0 kg/h PH$_3$ (177 mol/h) coming from a reservoir were compressed under a pressure of about 20 bars and introduced into the upper cooled portion of a pressure column. At the same time, a solution of 2,2'-azobis-(2-methylbutyronitrile) (VAZO® 67) in octene-1 (79.4 kg/h of which 0.4 kg=2 mol VAZO® 67) coming from a reservoir was introduced into the pressure column used as the reactor.

The reaction temperature in the pressure column was maintained between 80° and 85° C. by cooling. The crude product the filling level of which in the pressure column was controlled, was introduced into an autoclave with stirrer which was operated at 80° C. under a pressure of 3–4 bars. The reaction mixture the filling level of which was also controlled, was given into a further vessel with stirrer. The pressure column, autoclave with stirrer and vessel with stirrer had the dimensions necessary to ensure a residence time of about 7 hours which in turn is necessary to ensure the complete decomposition of the initiator at 80° C. The crude product (trioctylphosphine, octene) was continuously introduced with release of pressure into a low boiler column in which the octene in excess was separated under a vacuum of 200 millibars and at 160°–180° C. The octene was condensed, recycled and used again for preparing the initiator/octene-solution. The still product was removed from the distilling column through a valve. A specimen taken from the still product was analyzed gas-chromatographically. The following results were obtained:

Initiator decomposition product: 0.6% surface/surface
Octene-1: 0.5% surface/surface
Trioctylphosphine: 98.5% surface/surface $^{31}$P-NMR-spectroscopy failed to evidence the presence of monooctylphosphine or dioctylphosphine.

EXAMPLE 5

(Invention)

(a) Continuous preparation of sec.-butylphosphine 11.1 kg/h PH$_3$ (326 mol/h) was compressed in a two stage compressor under a pressure of 110 bars and introduced into a high pressure pipe reactor (volume=12 liters). At the same time, 8.9 kg/h butene-2 (cis/trans-mixture, 159 mol/hour) in which 30 g 2,2'-azobis-(2-methylbutyronitrile) (VAZO® 67) was dissolved per kg butene-2, coming from a reservoir, was introduced into the pipe reactor by means of a membrane dosing pump. The reaction zone was heated to 90° C. and the material in said zone was reacted. The exothermal reaction which commenced starting was so controlled by cooling with water that the temperature did not exceed 110° C. The crude product the filling level of which was controlled, was ultimately removed through a valve. The mean filling level was about 75%. This corresponded to a mean residence time of about 46 minutes at a mean density of 0.7 g/cm$^3$.

The product was then introduced into a vessel for release of pressure in which the bulk of the unreacted PH$_3$ and a portion of the butene-2 escaped in gas form. The liquid phase was given on to a separating column in which the residual low boilers (PH$_3$/butene) were removed. The united gas streams from release vessel and column were passed through a heat exchanger which was maintained at $-15°$ to $-20°$ C. by cooling with brine. The butene-2 was condensed and was recycled into the butene-reservoir. The PH$_3$ uncondensable under these conditions was recycled to the intake side of the compressor. At the onset of operation, a PH$_3$/butene-2-molar ratio of about 2:1 had been established. Under these reaction conditions, the conversion rate was 27%, based on the PH$_3$ used, and 56%, based on butene-2.

The still product was subjected to $^{31}$P-NMR-spectroscopy and the following results were obtained:
sec.-butylphosphine: 95.3 mol % ($\delta P = -114.7$ ppm)
di-sec.-butylphosphine: 4.4 mol % ($\delta P = -23.6/-28.7/-34.0$ ppm)
Components not identified: 0.3 mol %

(b) Comparative Example

The butene-2 was replaced by butene-1 which was reacted with PH$_3$ under the conditions described above. The product obtained was subjected to $^{31}$P-NMR-spectroscopy and the following results were obtained:
n-butylphosphine: 45.2 mol %
di-n-butylphosphine: 34.3 mol %
tri-n-butylphosphine: 20.5 mol %
(Wgt %: 31.2:37.7:31.1)
The conversion rate was 90.8%, based on butene-1.

(c) Continuous preparation of sec.-butyldioctylphosphine

The still product made as described under (a) above was reacted in two series-connected 640 liter-autoclaves with stirrer with octene-1 to give tert. phosphine. To this end, the still product taken from the separating column was introduced into the first reactor together with 102 kg/h of a 1 wgt % solution of VAZO ® 67 in octene-1 by means of a dosing pump.

The filling levels in the two reactors were controlled. The minimum temperature was 75° C. and the maximum temperature was 85° C. The reaction was effected under a pressure of 1.1–1.5 bars which was established by the nitrogen evolved during the decomposition of the initiator (VAZO ® 67). The crude product was introduced into a distilling column, in which the octene-1 in excess was separated at atmospheric pressure at still temperatures of about 210° C. (heating with steam, 16 bars). The olefin was recycled to the container used for preparing the initiator/octene-mixture.

The product taken from the still of the separating column was analyzed and the following results were obtained:
$^{31}$P-NMR:
94.6 mol % sec.-butyldioctylphosphine Bu$^s$Oct$_2$P
2.2 mol % di-sec.-butyloctylphosphine Bu$_2^s$OctP
2.2 mol % di-sec.-butylphosphine Bu$_2^s$PH
0.7 mol % sec.-butyloctylphosphine Bu$^s$OctPH
0.3 mol % components not identified
Gas-chromatography:
93.1% surface/surface sec.-butyldioctylphosphine
3.0% diethyl-dimethylsuccinic acid dinitrile (decomposition product of initiator)
1.7% di-sec.-butyloctylphosphine
1.0% di-sec.-butylphosphine
0.6% octene-1
0.3% sec.-butyloctylphosphine
0.3% components not identified.

We claim:

1. In the process for making tertiary alkylphosphines of the general formula R$_3$P, in which R stands for identical or different, linear, unsubstituted alkyl groups having 3 to 20 carbon atoms, where a secondary butyl group may however stand for one of the alkyl groups, by reacting hydrogen phosphide PH$_3$ with an alkene or alkenes in stoichiometric proportions or in stoichiometric excess, at elevated temperature and under increased pressure in contact with a radical-donator, the improvement which comprises: effecting the reaction in contact with 2,2'-azobis-(2-methylbutyronitrile) as the radical-donator in the absence of an alien solvent.

2. The process as claimed in claim 1, wherein tertiary alkylphosphines with straight alkyl groups are made by reacting an alkene-1 or alkene-1 blend with PH$_3$ in a stoichiometric ratio of 3:1 to 5:1, under a pressure of 1–80 bars, at a temperature of 75°–95° C. over a mean period of 4–24 hours in contact with 0.1–2 mol % 2,2'-azobis-(2-methylbutyronitrile) based on PH$_3$, and working up the crude trialkylphosphine by distilling it.

3. The process as claimed in claim 1, wherein tertiary alkylphosphines one of the alkyl groups of which is a secondary butyl group are made in two stages by reacting, in the first stage, butene-2 with PH$_3$ in a stoichiometric excess of up to 400 mol %, based on PH$_3$, *under a pressure of* 35–180 bars, at a temperature of 90°–120° C. over a mean reaction period of 0.1–7 hours in contact with 1–2 mol % 2,2'-azobis-(2-methylbutyronitrile), based on PH$_3$, and distillatively purifying the s-butylphosphine obtained, and then reacting, in the second stage, the said s-butylphosphine with an alkene-1 or alkene-1 blend in a stoichiometric excess of up to 1000 mol % total alkene-1, based on s-butylphosphine, under a pressure of 1–3 bars, at a temperature of 75°–95° C. over a mean reaction period of 4–24 hours and in contact with 2–6 mols 2,2'-azobis-(2-methylbutyronitrile), based on s-butylphosphine, and working up the crude s-butyl-di-n-alkylphosphine by distilling it.

4. The process as claimed in claim 1, wherein the reaction and distilling steps are carried out continuously.

5. The process as claimed in claim 1, wherein the 2,2'-azobis-(2-methylbutyronitrile) is dissolved in the alkene used as feed material or in the s-butylphosphine obtained as the intermediary product.

6. The process as claimed in claim 5, wherein the 2,2'-azobis-(2-methylbutyronitrile) is used as a 0.01–3.0 wgt % solution.

7. The process as claimed in claim 6, wherein the 2,2'-azobis-(2-methylbutyronitrile) is used as an olefinic solution.

8. The process as claimed in claim 2, wherein unreacted PH$_3$, butene-2 or alkene-1 separated in the distilling stages are recycled into the respective reaction stage.

9. The process of claim 1 wherein R has 4 to 10 carbon atoms.

* * * * *

UNITED STATES PATENT AND TRADEMARK OFFICE
CERTIFICATE OF CORRECTION

PATENT NO. : 4,757,156

DATED : July 12, 1988

INVENTOR(S) : Norbert Weferling, Georg Elsner, Hans-Werner Stephan, Friedrich-Karl Frorath It is certified that error appears in the above-identified patent and that said Letters Patent is hereby corrected as shown below:

On title page, item 73 should read: "Assignee: Hoechst Aktiengesellschaft, Frankfurt/Main, Fed. Rep. of Germany".

Signed and Sealed this

Twenty-fifth Day of July, 1989

Attest:

DONALD J. QUIGG

Attesting Officer

Commissioner of Patents and Trademarks